United States Patent [19]

Saaski et al.

[11] Patent Number: 6,136,611
[45] Date of Patent: Oct. 24, 2000

[54] ASSAY METHODS AND APPARATUS

[75] Inventors: Elric W. Saaski, Bothell; Charles C. Jung, Lynnwood, both of Wash.

[73] Assignee: Research International, Inc., Woodinville, Wash.

[21] Appl. No.: 08/904,421

[22] Filed: Jul. 31, 1997

[51] Int. Cl.[7] .................................................. G01N 33/552
[52] U.S. Cl. .............................. 436/527; 422/55; 422/57; 422/58; 422/82.05; 422/82.08; 422/82.09; 422/82.11; 435/287.1; 435/287.2; 435/288.7; 435/808; 436/164; 436/165; 436/172; 436/518; 436/525; 436/535; 436/805
[58] Field of Search ................................... 422/55, 57, 58, 422/82.05, 82.08, 82.09, 82.11; 435/287.1, 287.2, 808; 436/164, 165, 172, 518, 527, 525, 535, 805

[56] References Cited

U.S. PATENT DOCUMENTS

| | | | |
|---|---|---|---|
| 4,447,546 | 5/1984 | Hirschfeld | 436/527 |
| 4,558,014 | 12/1985 | Hirschfeld et al. | 436/527 |
| 4,582,809 | 4/1986 | Block et al. | 436/527 |
| 4,595,833 | 6/1986 | Sting . | |
| 4,654,532 | 3/1987 | Hirschfeld | 250/458.1 |
| 4,671,938 | 6/1987 | Cook | 422/57 |
| 4,716,121 | 12/1987 | Block et al. | 436/514 |
| 4,844,869 | 7/1989 | Glass | 422/68 |
| 4,852,967 | 8/1989 | Cook et al. | 350/96.29 |
| 4,909,990 | 3/1990 | Block et al. | 422/82.11 |
| 5,061,857 | 10/1991 | Thompson et al. | 250/458.1 |
| 5,152,962 | 10/1992 | Lackie | 422/681 |
| 5,242,797 | 9/1993 | Hirschfeld | 435/6 |
| 5,290,398 | 3/1994 | Feldman et al. | 156/651 |
| 5,359,681 | 10/1994 | Jorgenson et al. | 385/12 |
| 5,399,866 | 3/1995 | Feldman et al. | 250/458.1 |
| 5,430,813 | 7/1995 | Anderson et al. | 385/12 |
| 5,442,448 | 8/1995 | Knoll | 356/445 |
| 5,468,606 | 11/1995 | Bogart et al. | 435/5 |
| 5,492,674 | 2/1996 | Meserol | 422/82.08 |

FOREIGN PATENT DOCUMENTS

| | | |
|---|---|---|
| 0 535 690 | 4/1993 | European Pat. Off. . |
| WO 90 09574 | 8/1990 | WIPO . |

OTHER PUBLICATIONS

Anderson, George P. et al., "A fiber optic biosensor: combination tapered fibers designed for improved signal acquisition," *Biosensors & Bioelectronics* 8:249–256, 1993.

Anis, N.A. et al., "A Fiber–Optic Immunosensor for Detecting Parathion," *Analytical Letters* 25(4):627–635, 1992.

Gao, Harry H. et al., "Tapered fiber tips for fiber optic biosensors," *Optical Engineering* 34(12):3465–3470, 1995.

(List continued on next page.)

*Primary Examiner*—Christopher L. Chin
*Attorney, Agent, or Firm*—Christensen O'Connor Johnson & Kindness PLLC

[57] ABSTRACT

An optical assay apparatus is described which includes a light source module and an optical sensing element coupled by an interrogation module. The light source module produces light having propagation angles ranging from a lower, non-zero limit. This is accomplished by including an obscuration which blocks low propagation angle light. The sensing element includes a reflector portion and an sensing fiber portion. The reflector portion receives, as incident light, the light produced by the light source module and produces, as reflected light, light having an approximately constant propagation angle, preferably just less than the critical angle of the sensing fiber. The sensing element also includes a lens position which collimates signal recovery light collected by the sensing fiber. The interrogation module includes a window containing a light source optical fiber that transmits light from the light source module to the sensing element. The light source fiber has an angled end with a reflective surface to form a right-angle reflector and is embedded within the window in a slot containing an opaque material for absorbing back-scattered light. The sensing fiber may be appropriately adapted for evanescent-wave or surface plasmon resonance sensing operations.

39 Claims, 10 Drawing Sheets

OTHER PUBLICATIONS

Glass, Thomas R. et al., "Effect of numerical aperture on signal level in cylindrical waveguide evanescent fluorosensors," *Applied Optics* 26(11):2181–2187, 1987.

Golden, Joel P. et al., "Fluorometer and Tapered Fiber Optic Probes For Sensing In The Evanescent Wave," *Optical Engineering* 31(7):1458–1462, 1992.

Golden, Joel P. et al., "Portable multichannel fiber optic biosensor for field detection," *1997 Optical Engineering* 36(4),1008–1013, Apr. 1997.

Golden, Joel P. et al., "Ray Tracing Determination of Evanescent Wave Penetration Depth in Tapered Fiber Optic Probes," *Chemical, Biochemical, and Environmental Fiber Sensors IV 1796*:9–13, 1992.

Hale, Z.M. and F.P. Payne, "Fluorescent sensors based on tapered single–mode optical fibres," *Sensors and Actuators B.* 17:233–240, 1994.

Hobbs, J.R., "Fluorescence reveals toxins on antibody–coated fiberoptic probe," *Laser Focus World* 28(5):83–86, 1992.

Huber, W. et al., "Direct optical immunosensing (sensitivity and selectivity)," *Sensors and Actuators B.*6:122–126, 1992.

Jorgenson, R.C. and S.S. Yee, "A fiber–optic chemical sensor based on surface plasmon resonance," *Sensors and Actuators B.*12, (3):213–220, 1993.

Jung, C.C. et al., Chemical electrode surface plasmon resonance sensor, *Sensors and Actuators B.*32(2)143–147, 1996.

Ligler, F.S. et al., "Evanescent Wave Fiber Optic Biosensor," *Proc. Biosensors,* A.P.F. Turner, ed., pp. 308–315, 1992.

Rogers, Kim R. et al., "Acetylcholine Receptor Fiber–Optic Evanescent Fluorosensor," *Analytical Biochemistry* 182:353–359, 1989.

Wong, R.B. et al., "Reusable fiber–optic–based immunosensor for rapid detection of imazethapyr herbicide," in *Analytica Chimica Acta,* 279:141–147, 1993.

ASSAY METHODS AND APPARATUS

TECHNICAL FIELD

This invention relates generally to optical methods and apparatus for chemical and biochemical assays, and more particularly to fiber optics-based methods and apparatus for such assays.

BACKGROUND OF THE INVENTION

There exists a need for technology directed to economical field monitoring of toxins, explosives, and chemical contaminants. The United States has, for example, implemented a number of regulatory acts to protect its ecologies and its citizens from environmental pollution, and these acts mandate the monitoring of various chemical contaminants and other biohazards. Field-portable equipment is needed to supplement lab-based instrumentation, especially hardware that can identify and quantify with high specificity particular species of interest. One of the most promising strategies for performing such narrowly targeted field assays is based on sensors that harness natural immune and protective responses of animals and humans to identify specific compounds. Examples of such approaches include fiber optic evanescent wave sensors and surface plasmon resonance sensors.

An electromagnetic wave that is reflected at a dielectric interface produces an exponentially decaying electric field within the material on the opposite side of the interface. At optical frequencies this is termed an evanescent wave, and at radio frequencies this phenomenon is often called a "skin effect." Although the penetration depth of the evanescent wave is typically a small fraction of a wave length, many compounds of interest are themselves small molecules. Detecting these compounds can be accomplished by coupling sensor molecules 100 such as antibodies to the surface of the core of an optical fiber 102, as shown in FIG. 1A. In one competitive assay technique, fluorescently tagged antigen 104, together with the sample to be tested, is exposed to the coating on the fiber, and the tagged antigen competes for antibody bonding sites with non-tagged analyte 106 in the test sample. The evanescent field produced by light 108 passing through the fiber 102 then excites the fluorophores into light emission 110, and the fiber itself conveniently acts as a return waveguide for the fluorescent signal. In this example, the strength of the fluorescent signal is inversely related to the analyte concentration in the test sample. Alternatively, a non-competitive technique, such as a sandwich assay, can be used, in which case the fluorescent signal is directly related to the analyte concentration in the test sample.

For surface plasmon resonance sensing, FIG. 1B shows a thin layer of metal 110, such as gold, applied to a core portion 112 of an optical fiber 114 from which the cladding 116 of the fiber has been partly removed. The evanescent electric field produced by light 118 passing through the fiber 114 excites surface plasmon waves 120 on the outer surface of the metal 110. When white light is passed through the fiber 114, the excitation of a surface plasmon wave causes a dip in the spectrum of the light passing through the fiber, with the dip occurring at a resonance wavelength which is a function of the complex indices of refraction of the fiber core, the metal layer, and the solution surrounding the fiber, as well as the incidence angle of the light. Light passing through the fiber 114 can be returned by a mirror 122, or can be through-put (in the absence of a mirror) for optical processing and analysis, as is well known to those skilled in the art. Any change in the index of refraction of the solution is detectable, and molecules binding to the surface of the metal 110 can then be detected if they have an index of refraction that is different from the bulk solution. Coating the metal layer 110 with sensor molecules (not shown), which react with target analytes within a sample solution, then allows detection of reactions (such as antigen-antibody reactions and reduction-oxidation reactions) on the surface of the metal.

Fiber optic evanescent wave sensors are the subject of a number of U.S. patents, including the following, the disclosures of each being incorporated herein by reference: U.S. Pat. No. 4,447,546, to Hirschfeld et al., entitled "Fluorescent Immunoassay Employing Optical Fiber in Capillary Tube"; U.S. Pat. No. 4,558,014, to Hirschfeld et al., entitled "Assay Apparatus and Method"; U.S. Pat. No. 4,582,809, to Block et al., entitled "Apparatus Including Optical Fiber for Fluorescence Immunoassay"; U.S. Pat. No. 4,654,532, to Hirschfeld, entitled "Apparatus for Improving the Numerical Aperture at the Input of a Fiber Optic Devices"; U.S. Pat. No. 4,716,121, to Block et al., entitled "Fluorescent Assays, Including Immunoassays, with Feature of Flowing Sample"; U.S. Pat. No. 4,909,990, to Block et al., entitled "Immunoassay Apparatus"; U.S. Pat. No. 5,242,797, to Hirschfeld, entitled "Nucleic Acid Assay Method"; U.S. Pat. No. 5,061,857, to Thompson et al., entitled "Waveguide-Binding Sensor for Use With Assays"; U.S. Pat. No. 5,430,813, Anderson et al., entitled "Mode-Matched, Combination Taper Fiber Optic Probe"; U.S. Pat. No. 5,152,962, to Lackie, entitled "Immunoassay Apparatus"; U.S. Pat. No. 5,290,398, to Feldman et al., entitled "Synthesis of Tapers for Fiber Optic Sensors"; and U.S. Pat. No. 5,399,866, to Feldman et al., entitled "Optical System for Detection of Signal in Fluorescent Immunoassay." Fiber optic surface plasmon resonance sensors are the subject of U.S. Pat. No. 5,359,681 to Jorgenson et al., entitled "Fiber Optic Sensor and Methods and Apparatus Relating Thereto," the disclosure of which is incorporated herein by reference.

For evanescent wave sensors, it is desirable to optimize the magnitude of the evanescent electric field as well as to optimize the optical properties of the return path for the detected fluorescence. The above-identified patents describe numerous optimization approaches, including attempts to match the numerical aperture of various system components and to improve system numerical aperture. Numerical aperture is a measure of the largest angle, relative to the optical axis of a system, that a ray of light can have and still pass through the system. Each component in an optical system will have its own unique limiting numerical aperture, and the maximum system numerical aperture will be determined by the system component having the lowest numerical aperture. The system numerical aperture is a key parameter in optical sensing since transferred power is typically proportional to its square. Good design practice and cost efficiencies require system components to have matching numerical apertures.

One well-known approach of matching numerical apertures employs tapered or cone-shaped waveguides. In addition to providing numerical aperture matching, tapering the active, analyte-sensitive portion of the optical fiber maintains a substantial fraction of the input light near the critical angle, thereby maintaining a high magnitude evanescent field. However, there is also a constant loss of light along the sensor fiber as the taper acts upon rays that are already only weakly guided and causes them to exceed the critical angle.

In order for white light to propagate in an optical fiber used in connection with a surface plasmon resonance sensor, the fiber must have a large enough diameter to support the longest wavelength of light. Also, a large diameter fiber propagates higher numerical aperture light, which makes it easier to excite surface plasmon waves in metal films of thicknesses readily fabricated by conventional processes. As a consequence, multi-mode fibers are used which propagate light over a range of angles. However, this range of angles results in a less distinct resonance effect, because each angle of propagation results in a different resonance wavelength.

FIG. 2A shows the theoretical resonance curves for various propagation angles relative to the optical axis of the fiber core, assuming a 55 nm thick layer of gold on a silica optical fiber core immersed in water. The overall resonance detected is a superposition of the resonance effects for each of the various angles of propagation. FIG. 2B shows the integration of individual theoretical resonance curves for propagation angles from 0 to 23.6 degrees, assuming a sine-squared distribution of optical power at the various propagation angles. The significant signal degradation associated with current approaches to surface plasmon resonance sensing is seen by comparing the resonance curve of FIG. 2B with the individual resonance curve of, for example, 23.6 degrees in FIG. 2A.

Although fiber optic evanescent wave and surface plasmon resonance sensors show great promise for use in field-portable assay equipment, those skilled in the art understand that the current technology is less than optimal in a number of respects, including those disadvantages identified above.

SUMMARY OF THE INVENTION

In accordance with the present invention, an optical assay apparatus includes a light source module and an optical sensor. The light source module produces light having a range of propagation angles. The sensor includes a light adjusting portion and an assay sensing portion. The light adjusting portion receives the light produced by the light source module and provides light having a propagation angle that is substantially constant to the assay sensing portion.

In one embodiment, the light source module produces light having propagation angles ranging from a lower, non-zero limit. This may be accomplished by including an obscuration which blocks light having propagation angles below this limit. In one embodiment, the light adjusting portion of the sensor may include a reflector which receives, as incident light, the light produced by the light source module and produces, as reflected light, the light having a substantially constant propagation angle. The assay sensing portion of the sensor may be a waveguide coated with sensor molecules suitable for performing evanescent wave sensing operations, or may be a waveguide coated with a thin metallic film suitable for performing surface plasmon resonance sensing operations.

In one embodiment, the sensor may be coupled with the light source module by an interrogation module which includes a window in which a waveguide is integrated. The waveguide transmits the light produced by the light source module to the sensor. The waveguide may be an optical fiber with an angled end having a reflective surface to create a right-angle reflector. The waveguide may be embedded in the window in a slot containing an opaque material to prevent back-scattering of excitation light from the waveguide into optical components included within the interrogation module.

DETAILED DESCRIPTION OF THE INVENTION

An optical assay apparatus and method is described, with certain specific details set forth in order to provide a thorough understanding of various embodiments of the present invention. However, one skilled in the art will understand that the present invention may be practiced without these details. In other instances, well-known structures and operations are not shown or discussed in detail in order to avoid obscuring the description of the embodiments of the invention.

Figure 3:
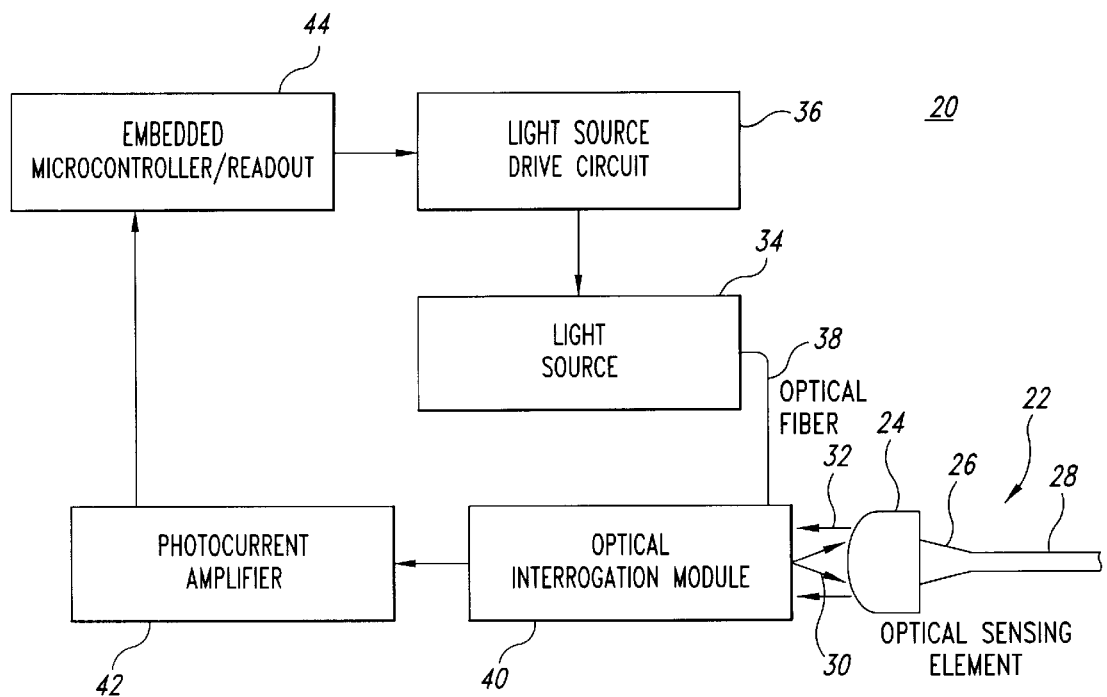
FIG. 3 is a functional block diagram which depicts an assay system in accordance with an embodiment of the present invention.

FIG. 3 is a functional block diagram which depicts an assay system 20. An optical sensing element 22 includes a lens portion 24, a reflector portion 26, and a sensing waveguide or fiber portion 28, as will be described in further detail below. The sensing element 22 receives excitation light 30 and returns signal recovery light 32. The excitation light 30 is produced by a light source module 34, under control of a drive circuit 36. The light source module 34 provides the excitation light via a waveguide or optical fiber, such as source fiber 38. An interrogation module 40 receives the signal recovery light 32, and can also advantageously optically couple the sensing element 22 with the excitation light 30 transmitted via the source fiber 38. The optical interrogation module 40 includes optical devices, such as lenses, and transducers, such as photodetectors, to produce an electrical signal functionally related to the signal recovery light 32. The electrical signal is amplified by photocurrent amplifier 42 which provides the amplified signal to a microcontroller 44. The microcontroller 44 then interprets the amplified signal, and provides the sensing operation results in the form of a readout or printout, or stores the results for later analysis. The microcontroller 44 also can control operation of the light source drive circuit 36.

Those skilled in the art will appreciate that the assay system depicted in FIG. 3 is a simplified block diagram showing components whose configuration and function is well-known. Details concerning portions of the light source module 34, the optical interrogation module 40, and the sensing element 22 will be described below in connection with the various embodiments of the present invention. Further details regarding the other functional blocks shown in FIG. 3 need not be described herein for those skilled in the art to practice the present invention.

Figure 4:
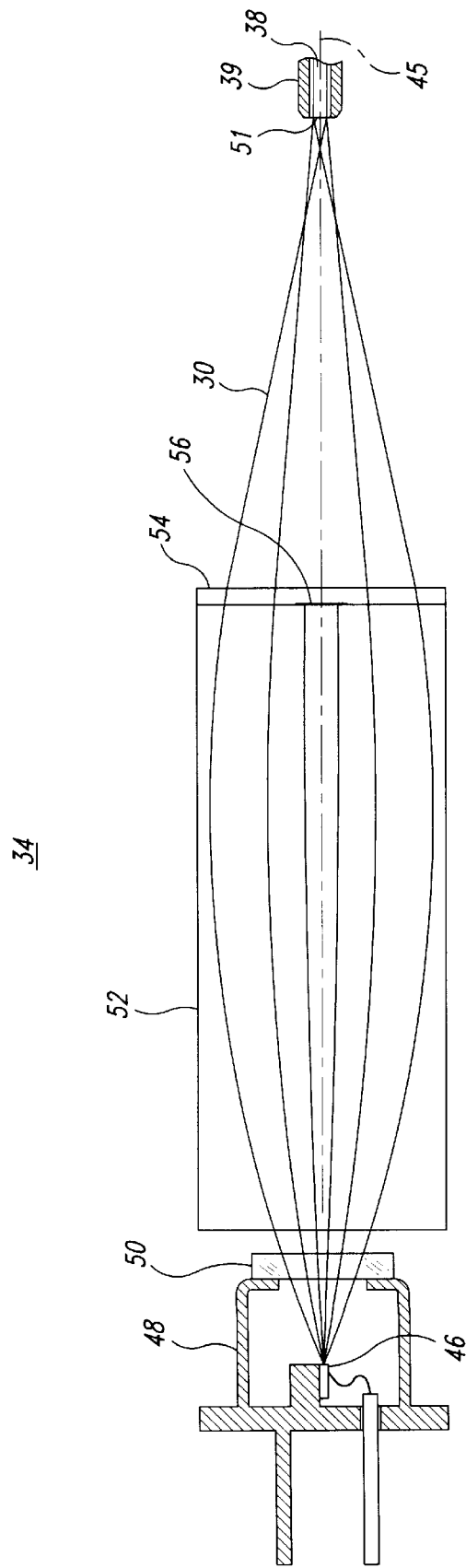
FIG. 4 depicts a portion of a light source module included in the assay system of FIG. 3.

FIG. 4 depicts a portion of the light source module 34 of FIG. 3. The figure depicts a cross-section taken along an optical axis 45. A light source, such as a laser diode 46, is included within a source housing 48 having a window 50. The laser diode 46 produces the excitation light 30 which is focused onto an end 51 of the source fiber 38 by a numerical aperture-adjusting lens 52. The source fiber 38 is held by an optical fiber ferrule 39 used for positioning the end 51 of the fiber at the focal point of the numerical aperture-adjusting lens 52. The source fiber 38 then transfers the excitation light to the sensing element 22, for example, as shown in FIG. 3.

In one embodiment, the laser diode 46 is a 635 nm wavelength, 5 mW output solid-state laser diode, and the numerical aperture-adjusting lens 52 is a 3 mm diameter, 0.25 pitch graded refractive index (GRIN) lens. The source fiber 38 is a 200 micron core-diameter optical fiber, which is preferably made of a transmission material such as glass or quartz, since such material generates minimal self-fluorescence and has low scattering losses. However, plastic fibers or other waveguides may be suitable, especially if the distance from the light source module 34 to the sensing element 22 (see FIG. 3) is less than a few meters. In this embodiment, the GRIN lens transforms the approximately 0.4 to 0.6 numerical aperture of the laser diode 46 to approximately 0.22, in keeping with the comparatively low maximum numerical aperture of quartz fibers. A thin (approximately 0.15 mm) transparent glass disk 54 is bonded to the GRIN lens 52 by a transparent adhesive, and includes a circular obscuration 56 of approximately 0.75 mm diameter positioned symmetrically about the optical axis 45. The effect of the obscuration 56 is to eliminate low propagation angle rays from being input to the source fiber 38. If the source fiber 38 is not bent so severely as to promote internal mode conversion, and does not contain large numbers of scattering centers, then light exiting the fiber will have the same angular characteristics as light entering the fiber.

Figure 5:
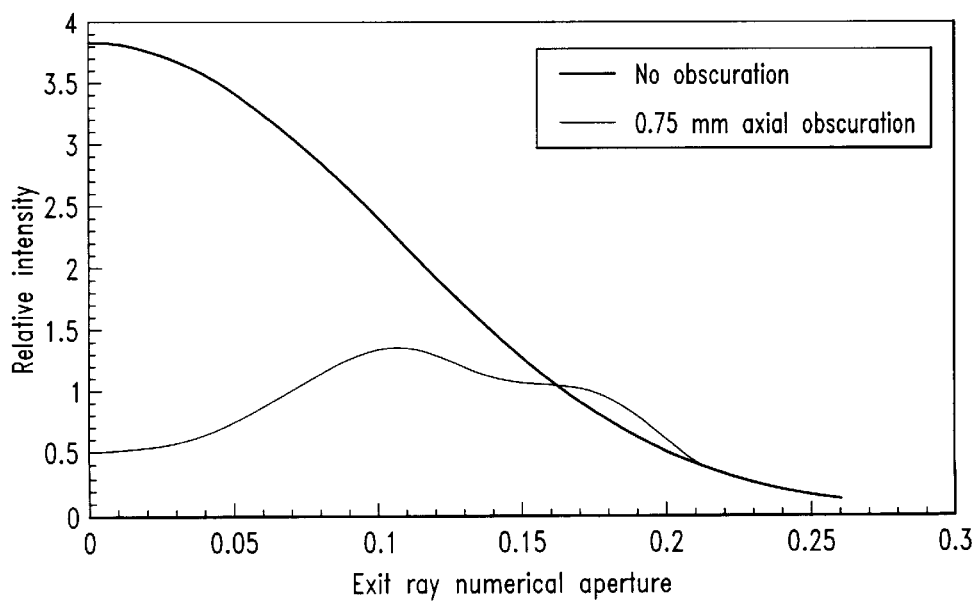
FIG. 5 is a graph which depicts the improved light distribution provided by the light source module of FIG. 4.

FIG. 5 is a graph which shows measurements of the angular distribution of the light exiting from the source fiber 38, with and without the obscuration 56. These measurements correspond to the light source module 34 and source fiber 38 of the particular construction described above. Clearly, the obscuration 56 provides an angular distribution of light with the lower propagation angle rays largely removed, the advantage of which will become apparent in the discussion below. For purposes of convenient presentation, propagation angles relative to the optical axis 45 (see FIG. 4) are represented as numerical aperture values in the graph of FIG. 5.

Figure 6A:
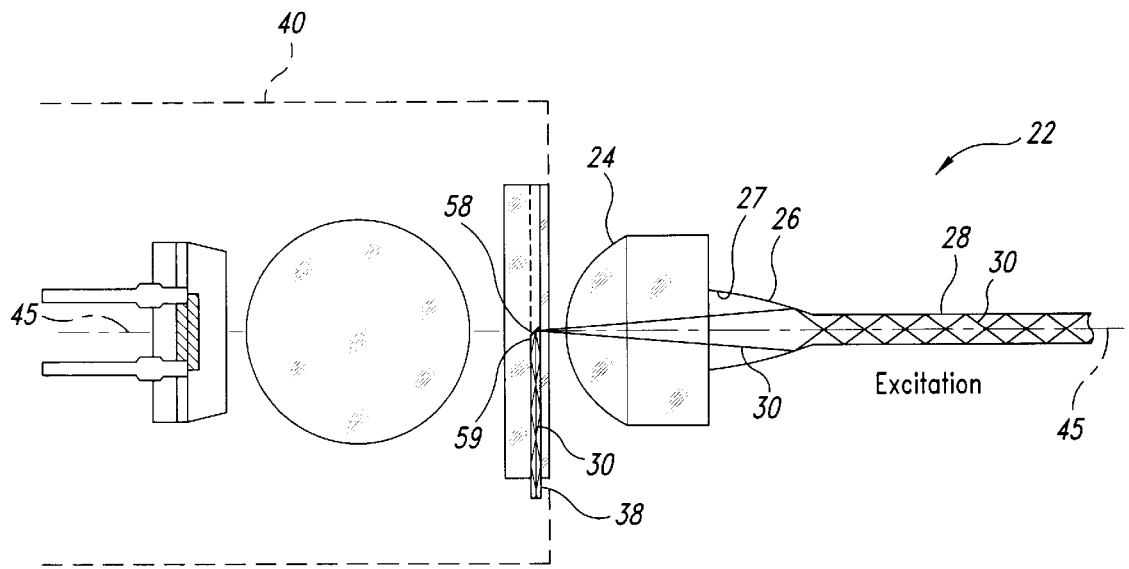
FIG. 6A depicts a portion of an optical interrogation module and of an optical sensing element included in the system of FIG. 3, and shows an excitation light path.

FIG. 6A shows the excitation light 30 passing through the source fiber 38 to a right-angle reflector 58 constructed on a distal end 59 of the fiber. The excitation light 30 then passes into the lens portion 24 of the sensing element 22, reflects off a reflective surface 27 of the reflector portion 26, and passes into the sensing fiber portion 28. The sensing fiber portion 28 may be a core portion of an optical fiber from which the cladding has been removed. Alternatively, the sensing fiber 28 may be a plastic fiber, or any of a variety of suitably adapted waveguide configurations.

Figure 6B:
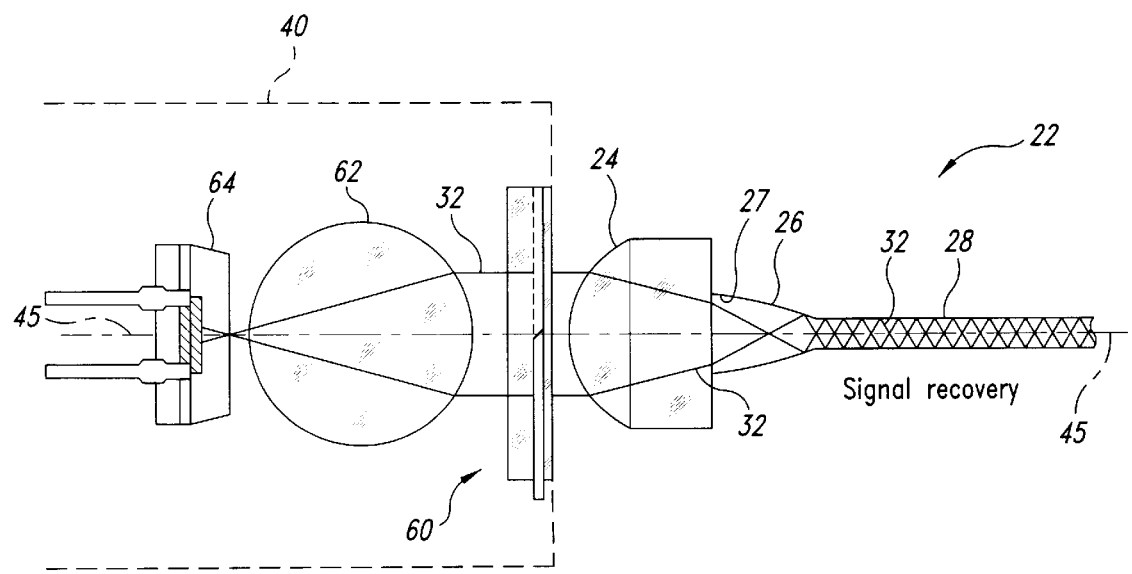
FIG. 6B depicts the portions of the interrogation module and of the optical sensing element of FIG. 6A, and shows a signal recovery light path.

FIG. 6B depicts the return of signal recovery light 32, such as from evanescent field-induced fluorescence, through the sensing fiber 28, reflecting off the reflector 26, refracting through the lens 24, and passing into the interrogation module 40 (also see FIG. 3) through an interrogation window 60. Once inside the interrogation module 40, the signal recovery light 32 is focused by a lens, such as a sapphire ball lens 62, onto a transducer, such as a photodetector 64.

Figure 7A:
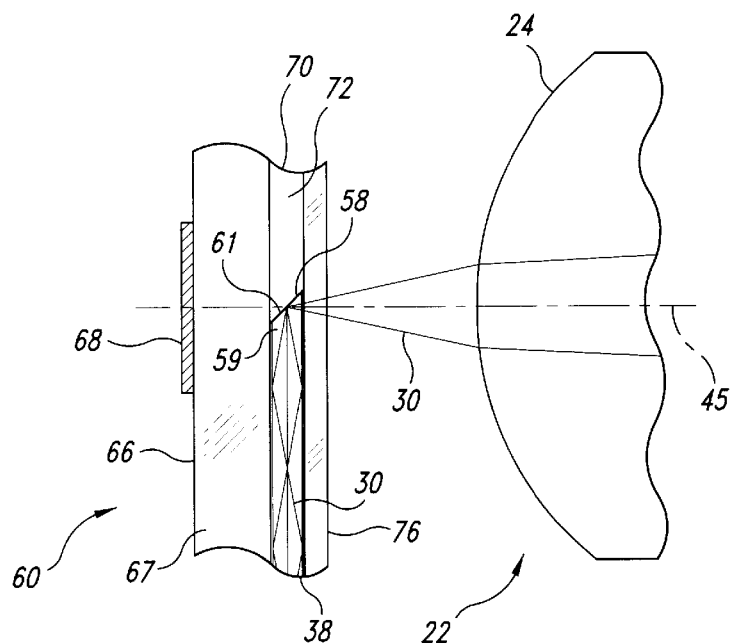
FIG. 7A is a side view which depicts an embodiment of an interrogation module window included in the optical interrogation module of FIG. 6A.

FIG. 7A shows greater details of one embodiment of the interrogation module window 60. The distal end 59 of the source fiber 38 is polished to a 45° mirror finish, and coated with a reflective film 61, to form the right-angle reflector 58. This portion of the source fiber 38 is integrated within the interrogation module window 60, as described in detail herein. The right-angle reflector 58 is oriented so that light within the source fiber 38 emerges from the window 60 generally perpendicular to the window surface, with a numerical aperture of, for example, 0.22.

The interrogation module window 60 includes a dichroic laser-line rejection filter film 66 deposited onto one face of a glass plate 67. The primary function of the filter film 66 is to exclude any flare light associated with the excitation light 30 from reaching the optical components included within the interrogation module 40, while providing an unimpeded path for the longer wavelength fluorescent signal recovery light 32 (see FIGS. 6A and 6B). It is desirable that the filter film 66 attenuate any laser flare light by a factor of $10^3$ to $10^4$. Any of numerous types of filter designs may be employed, such as thin-film interference filters. A glass plate with specified filter characteristics can be purchased from Optical Coating Laboratories of Santa Barbara, Calif. Currently, the simplest and most cost-effective filter is a long-pass dichroic filter which transmits wavelengths above a critical wavelength and blocks wavelengths below that critical wavelength.

For the exemplary 635 nm laser source described above, a long-pass filter with a 50% blocking wavelength in the range of 650–670 nm will perform satisfactorily. Alternatively, a glass or plastic window with suitable colorant that is highly absorptive at the laser wavelength may be used, separately or in combination with a dichroic filter. A circular obscuration 68 of, for example, approximately 1.5 mm diameter is painted or coated onto the exterior surface of the filter film 66. The obscuration 68 augments the filter film 66 by blocking any back-reflected excitation light 30 which might be reflected off the lens portion 24 of the sensing element 22.

Figure 7B:
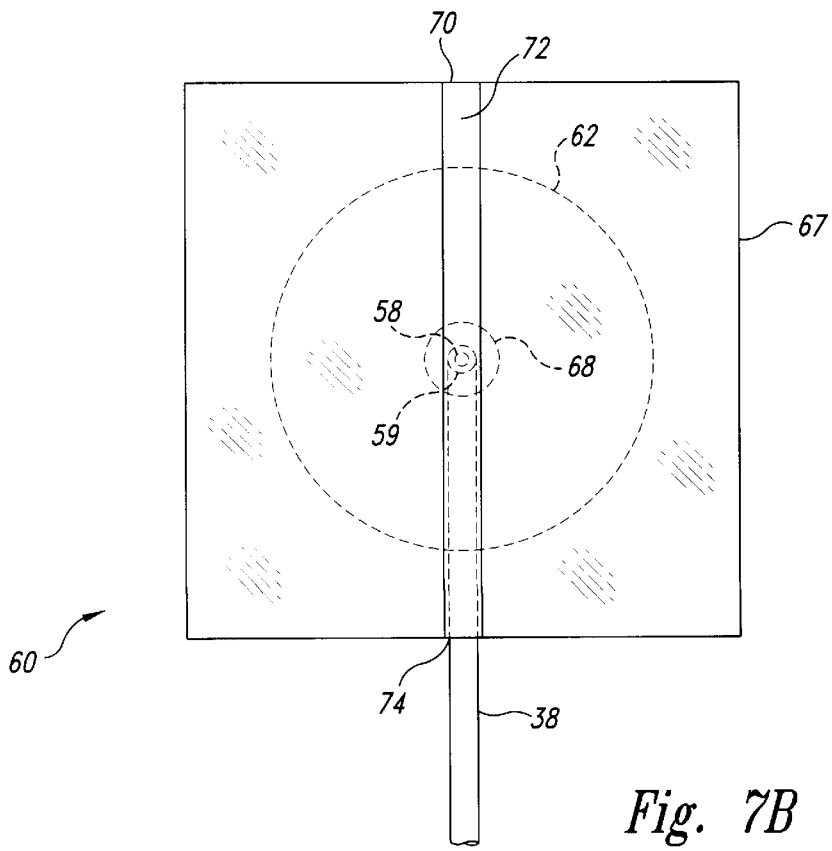
FIG. 7B is a front view of the interrogation module window of FIG. 7A.

Referring to both FIGS. 7A and 7B, a groove 70 is cut into the glass plate 67 on the side opposite the dichroic filter film 66. This groove may be cut by using a high-speed, water-cooled diamond saw. The slot 70 is then filled with a highly opaque material 72, such as 320 epoxy from Epoxy Technologies of Billerica, Mass. A second, narrower slot 74, equal to the width of the source fiber 38, is then made in the opaque material 72, taking care to position the slot 74 so that it does not break through the opaque material 72 at any point along the length of the slot 74. The source fiber 38 is then positioned in the slot 74 so that it is emitting light at the correct position and in the correct direction, and a thin glass cover plate 76 is pressed against the groove window face to preserve the fiber's position. A transparent material, such as UV adhesive P92 from Summers Optical of Fort Washington, Pa., is then wicked into the void area surrounding the entrapped source fiber 38 to remove any air, and the adhesive is cured.

Both the adhesive and cover plate 76 should be selected to have refractive indices that are approximately the same as the cladding of the source fiber 38 to minimize aberration in the projected beam. Since the excitation light 30 must, upon reflection from the right-angle reflector 58, pass through the cylindrical wall of the source fiber 38, the fiber's wall would otherwise act as a cylindrical lens and distort the shape of the emitted excitation light beam. The opaque material 72, together with the obscuration 68, absorbs any excitation light spilled from defects in the mirror coating at the right-angle reflector 58 or reflected at the interface where the excitation light 30 first enters the lens portion 24 of the sensing element 22.

The sensing element 22, discussed above in connection with FIGS. 3, 6A and 6B, can be advantageously formed as a single piece, such as by injection molding of polystyrene. As shown in FIG. 6A, the excitation light 30 entering the sensing element 22 first encounters the surface of the lens portion 124, which may be any of a number of suitable configurations such as a spherical or paraboloidal lens. The primary function of the lens portion 24 is to collimate signal recovery light 32, as shown in FIG. 6B. However, the lens portion 24 also plays a secondary role as regards the excitation light 30, essentially displacing the effective origin of the excitation light along the optical axis 45.

As described above in connection with the current state of the art, light provided by an excitation source is composed of an equilibrium distribution of ray propagation angles and tapered fiber sections are oftentimes used to match numerical apertures to a level compatible with a sensing fiber when immersed in a fluid sample. However, this approach wastes significant input energy because the angular characteristics of most of the light rays are such that they contribute only weakly to the evanescent electric field strength. Other attempts use a taper along the full length of the sensing fiber, thereby transforming low propagation angle rays at some point along the fiber to higher propagation angle rays that can contribute to the evanescent electric field. However, for these rays at lower angles to be productive, rays initially having larger propagation angles must necessarily have been lost. The continual upgrading of lower propagation angle rays by the fiber taper is obtained at the penalty of excitation light leakage along the fiber's length. This means that assay sensitivity is variable along the fiber, which can cause calibration problems. Also, light leaking from the fiber into the exterior fluid could lead to fluorescence pick-up from the sample fluid itself, instead of solely from bound fluorophore molecules.

Ideally, all incoming excitation rays should be very nearly at the critical angle of a sensing fiber to maximize the evanescent electric field strength, thereby maximizing the fluorescence output by any fluorophore molecules bound to the fiber. Also, the sensing fiber should be of essentially constant diameter so that the sensitivity per unit length is constant, and with light leakage to the external environment minimized. As a practical matter, a slightly tapered sensing fiber may be required as a consequence of manufacturing processes, such as fabrication by injection molding. Typically, a taper of approximately 0.02° is sufficient to assure defect-free removal of a fiber from an injection mold, and such a taper has essentially negligible optical effects. Embodiments of the present invention can provide a near-ideal situation, primarily due to characteristics of the reflector portion 26 of the sensing element 22.

Referring to FIG. 6A, the reflective surface 27 of the reflector portion 26 is constructed with an axial profile such that all rays emitted from the end of the source fiber 38 are reflected at the same angle with respect to the optical axis 45 of the sensing element 22. In other words, all rays in the sensing fiber 28 have the same propagation angle—a highly desirable feature for an evanescent-wave-based sensor. Assuming the light source (i.e., the right-angle reflector 58 at the end of the source fiber 38) is approximately a point source, and that the angular distribution of the light emitted from that source falls within certain limits (discussed below), the shape of the requisite reflecting surface 27 can be readily mathematically derived. In practice, the point source requirement is not a difficult condition to meet, since optical fibers are available with core diameters of as small as 3 μm, and it is also possible to simply increase the relative size of the sensing element 22. As a practical matter, it has been found through experimentation that if the diameter of the sensing fiber 28 is about four times larger than that of the source fiber 38, then the point source condition is approximately obtained.

Figure 8:
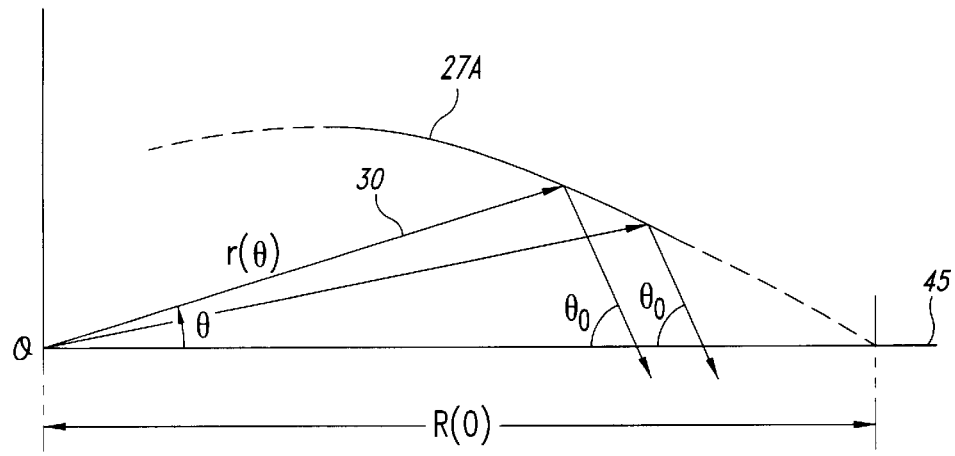
FIG. 8 depicts the geometry of a reflector portion included in the optical sensing element of FIGS. 6A and 6B.

The shape of the desired reflective surface 27 is defined by a rotation about the optical axis 45 of a curve 27A shown in FIG. 8. With a point source of light assumed at an origin O, the curve 27A can be described in accordance with the depicted polar coordinates as $$r(\theta) = R(0) \cdot \frac{(1 - \cos(\theta_0))}{(1 - \cos(\theta + \theta_0))},$$

where $r(\theta)$ is the distance from the origin O to the curve 27A, and $\theta$ is the angle between the excitation ray line 30 and the optical axis 45. The angle $\theta_0$ is the desired constant exit angle relative to the optical axis, and R(0) is the distance from the origin to the curve 27A at $\theta=0$ degrees.

Figure 9:
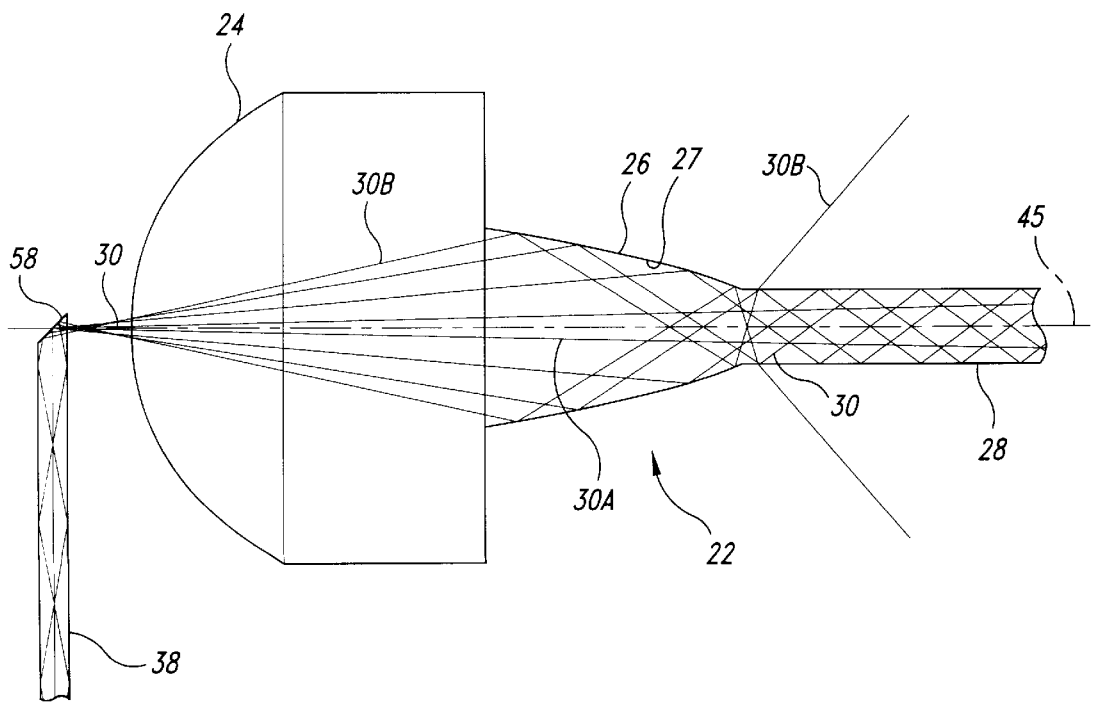
FIG. 9 is an optical ray tracing which depicts the effect of the reflector portion of FIG. 8 on excitation light rays directed at various angles.

Referring to FIG. 9, it is apparent that the reflective surface 27 performs as desired only on rays within a certain range of propagation angles. As shown, those excitation rays 30A propagating at a small angle relative to the optical axis 45 pass directly into the sensing fiber portion 28. Those rays 30B propagating at relatively large angles to the optical axis reflect off the reflective surface 27 a second time and are refracted out of the sensing element 22. However, even within these propagation angle constraints, it is not difficult to collect and direct 80–90% of the rays into the sensing fiber portion 28 at the desired angle $\theta_0$.

The numerical aperture for a polystyrene waveguide immersed in water is about 0.856. Light rays directed at larger propagation angles will leak into the surrounding water. The greatest evanescent electric field strengths will then be produced when the excitation light propagation angle is very near the critical angle. The refractive index of polystyrene in the 600–700 nm waveband is about 1.584

(i.e., a critical angle of about 32.7° relative to the optical axis). As a matter of practical design, however, it may well be better to use a lower propagation angle to compensate for effects of possible misalignment associated with manufacturing tolerances, etc. A design propagation angle of approximately 2° less than the critical angle is readily achieved and yields satisfactory results.

Figure 10:
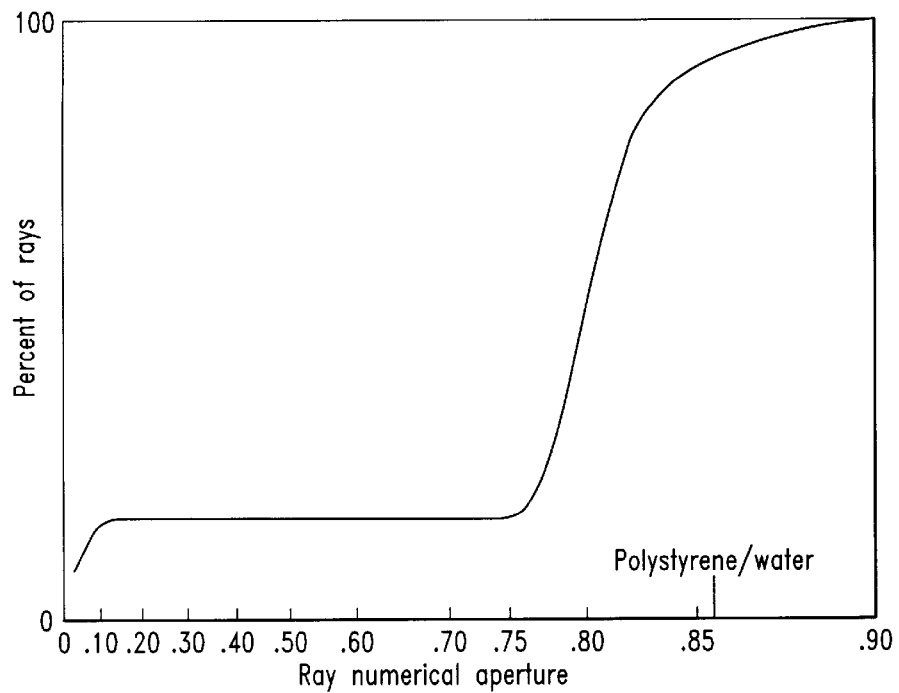
FIG. 10 is a graph which depicts the angular distribution of light rays acted on by the reflector portion of FIG. 8.

FIG. 10 depicts the cumulative angular distribution of rays entering into the sensing fiber portion 28 of the sensing element 22, as modeled with a commercial ray-tracing program, Opticad™. The particular sensing element modeled is constructed with the dimensions shown in FIG. 11, and with a 200 µm diameter source fiber 38 placed 0.5 mm distant from the facing surface of the lens portion 24 of the sensing element. For purposes of modeling simplicity, it is assumed that the source fiber 38 transports rays with a uniform distribution of ray angles up to a limiting numerical aperture of 0.22.

Figure 11:
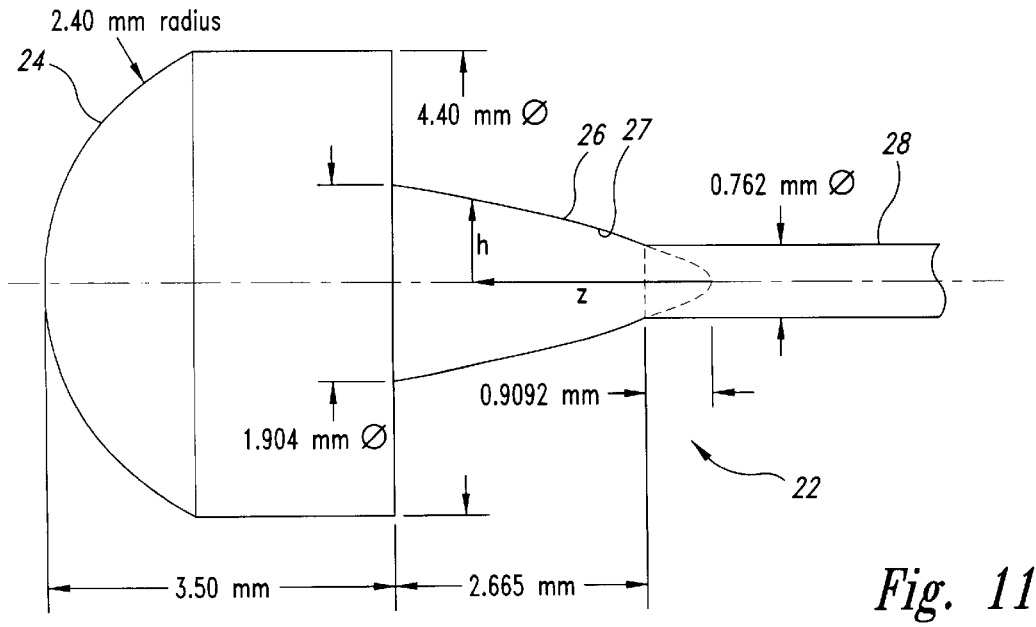
FIG. 11 identifies specific geometries of lens and reflector portions of an optical sensing element in accordance with a presently preferred embodiment of the invention.

FIG. 11 depicts the specific geometries of the integrated lens portion 24 and the reflector portion 26, which may be described with reference to a lensmakers equation, $$z(mm)=7.59178h^2-1.130917h^4+15.184765h^6-1.276721h^8+3.500005h^{10},$$

which will be understood by those skilled in the art.

As shown in FIG. 10, the fraction of rays at small propagation angles is quite modest. Most rays are tightly clustered around the design propagation angle (expressed as a numerical aperture value of 0.81), and over 84% of the rays launched into the fiber portion 28 of the sensing element 22 have propagation angles expressed as numerical aperture values in excess of 0.75. Approximately 16% of the rays have propagation angles expressed as numerical aperture values less than 0.15, representing those rays that passed through the aspherical reflector section 26 at a low propagation angle, and hence were not acted upon by the reflector 26.

A further improvement is provided by the central obscuration 56 used in the light source module 34 shown in FIG. 4. Notably, FIG. 10 does not include the effect of this obscuration 56, which would substantially block all of the lower propagation angle rays. Because the low propagation angle light does not materially contribute to the evanescent electric field strength, it is of little value for sensing signal generation. It can, however, be a significant source of non-signal background light that must be rejected by the interrogation module 40 (see FIG. 6B). Such background flare light can come from several sources, such as tramp fluorescence caused by a radiation of the bulk sensor material or trace impurities within it, or, alternatively, excitation light leaking into the interrogation module 40 itself. Excitation rejection filters, such as the dichroic filter film 66 (see FIG. 7A), cannot be made 100% efficient, and high background light may also be caused by excitation light that has been back-reflected from particles in the waveguide or from waveguide surface imperfections. By removing low propagation angle excitation light from the system, the amount of non-signal background light in the interrogation module 40 is correspondingly reduced with little effect on the evanescent electric field excitation of surface-bound fluorophores.

Referring to FIG. 6B, it is desirable that signal recovery light 32 be collimated before it enters the interrogation module 40. The performance of the dichroic filter film 66 (see FIG. 7A) typically deteriorates if rays impinge at angles more than about plus or minus 10° from the design incidence angle. Since the fluorescence process generates an isotropic distribution of ray angles from any fluorophore site, it is also desirable to collimate the wide angular distribution of rays so that they can be directed to a small, low-noise photodetector.

The fraction of signal recovery light 32 that has comparatively low propagation angles exits the sensing fiber portion 28 and passes directly through the lens 24 of the sensing element 22. The surface of the lens portion 24 and its axial placement are such that these rays emerge from the sensing fiber 28 approximately at the focal point of the lens, thereby exiting from the lens in a collimated condition. However, a second and typically larger fraction of the signal recovery light 32 exits the sensing fiber portion 28 at large propagation angles. Many of these rays then advantageously strike the reflecting surface 27 of the reflector 26, which reflects this higher propagation angle light into the lens 24, and thereafter into the optical systems included within the interrogation module 40, thereby collecting a substantial portion of recovered signal light that would have otherwise been lost. Ray modeling studies indicate that over 90% of the signal recovery light emitted from the sensing fiber 28 reaches the photodetector 64.

The light that passes through the interrogation module window 60 is focused by a short focal length lens onto a suitable low-noise photodetector 64. Any lens of high light-gathering power may be used, with a particularly effective and compact design being created by a sapphire or high-index glass sphere of 1 to 10 mm diameter. Sapphire spheres of optical quality may be purchased from Edmund Scientific of Barrington, N.J. A solid-state photodiode is a suitable photodetector 64, since it is small, consumes no power, and has low noise. Light falling on the photodetector 64 is then converted to a photocurrent, which in turn is converted to a voltage using standard small-signal electronic amplification methods, such as synchronous detection. Using a 6 mm sapphire ball lens; a low-noise photodiode, type S4707-01 from Hammatsu, Inc. of Bridgewater, N.J.; and a synchronous detection amplification technique operating at an optimum chopping frequency of 135 Hz; an extremely favorable photocurrent sensitivity of 0.025 pA was realized.

Figure 12:
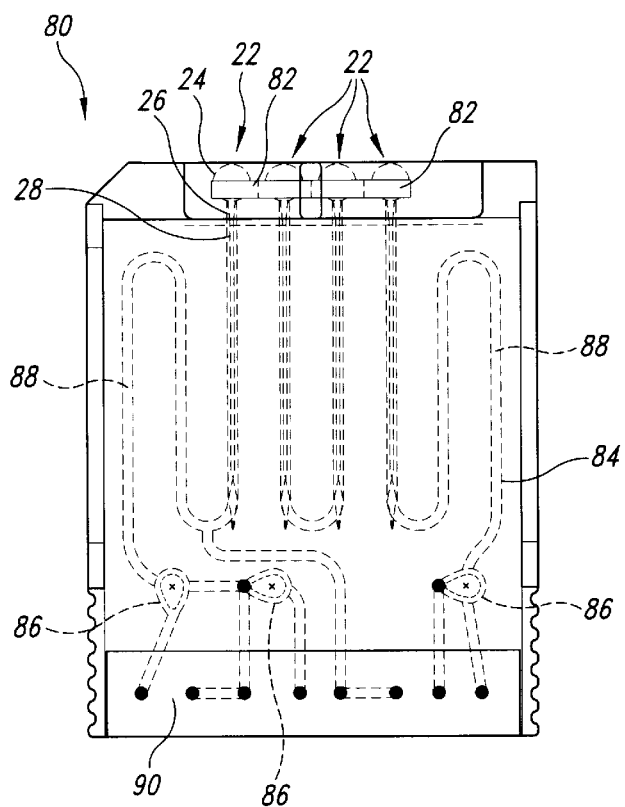
FIG. 12 depicts an assay coupon including the optical sensing element of FIGS. 6A and 6B.
Figure 13:
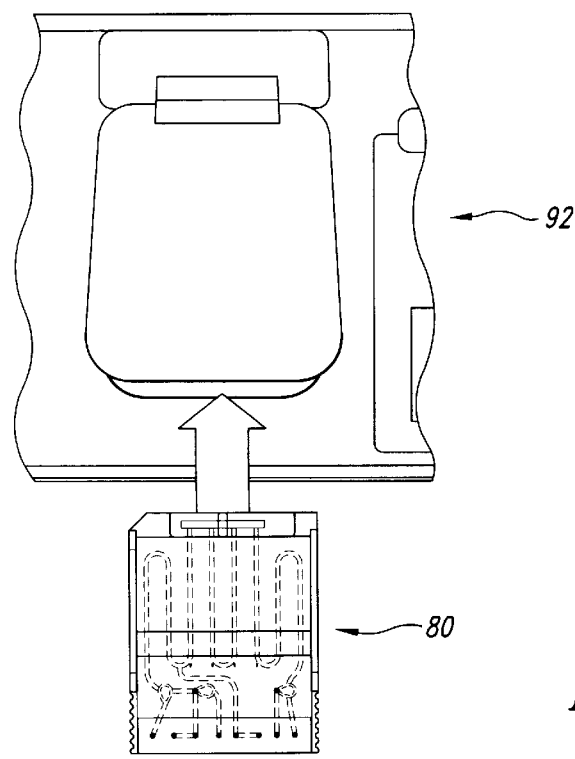
FIG. 13 depicts an assay unit in which the assay coupon of FIG. 12 may be inserted.

FIG. 12 depicts a disposable assay card or coupon 80 having four of the sensing elements 22. Each of the sensing elements 22 depicted in the figure also includes a tab 82, which is preferably of integral, one-piece construction with the lens 24, reflector 26, and sensing fiber 28. The tab 82 assists in manipulation and placement of the sensing element 22 during fabrication of the coupon 80. The coupon 80 includes a plurality of valves 86 for controlling the flow of sample and reagent fluids into an assay reaction vessel, such as a multiple flow tube or channel configuration 88, in which the sensing fibers 28 are positioned. These fluids are introduced into the flow channels 88 through a needle septum 90. As shown in FIG. 13, the coupon 80 can be inserted into an assay unit 92, in which other components of the assay system 20 of FIG. 3 are included, along with on-board reservoirs (not shown) for buffer, reagent, and waste fluids, as will be understood by those skilled in the art.

Although much of the discussion above focuses on applications to evanescent-wave-based sensors, those skilled in the art will appreciate that the sensing element 22 may be suitably adapted for use in a surface plasmon resonance sensor. The ability to convert various propagation angles of light into an approximately constant propagation angle for transmission into a optical fiber is particularly advantageous for surface plasmon resonance techniques. As described above, in connection with the current state of the art, the detected resonance spectrum for currently available surface plasmon resonance sensors is the superposition of resonance spectra associated with light at various propagation angles transmitted down the sensing fiber. If, instead, light of essentially a single propagation angle is used, the resonance effect in the transmitted spectrum is much better defined, is more easily detected, and affords better quantitative analysis.

Figure 1A:
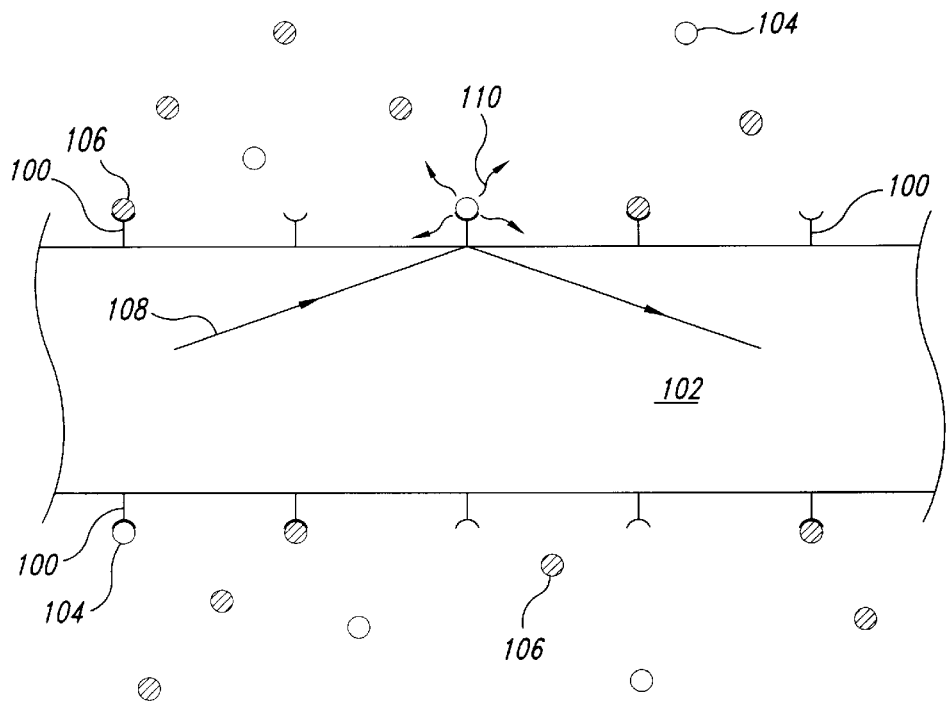
FIG. 1A depicts an optical fiber adapted for use in evanescent wave sensing operations in accordance with the prior art.
Figure 1B:
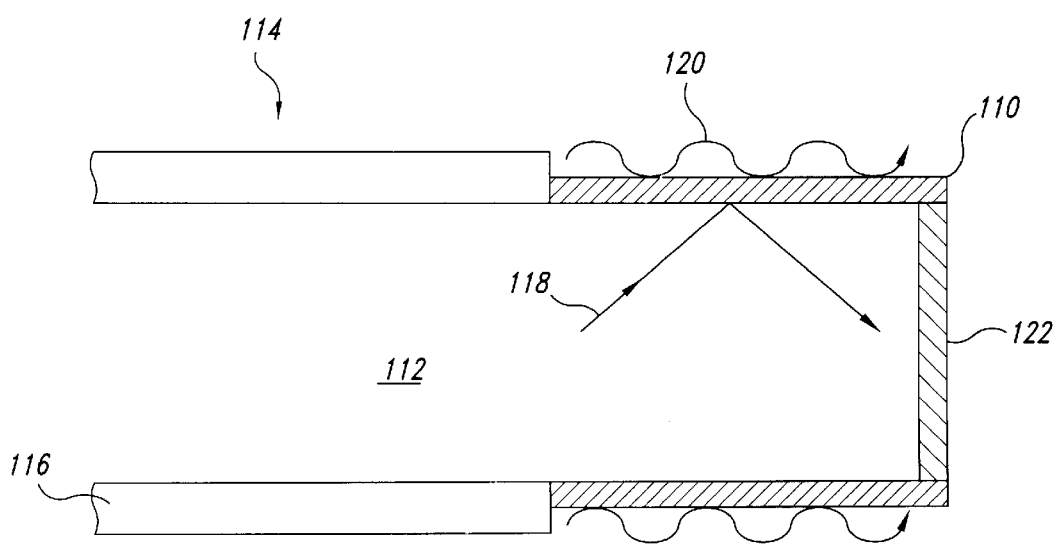
FIG. 1B depicts an optical fiber adapted for use in surface plasmon resonance sensing operations in accordance with the prior art.

The assay system described above is readily adapted for use with surface plasmon resonance sensing operations. A light source module producing white light can be coupled to the sensing element 22 by a source fiber, an interrogation module, and an interrogation window, of substantially similar configuration to the above-described source fiber 38, interrogation module 40, and interrogation module window 60. If the surface plasmon resonance sensor fiber 114 includes a mirror 122 for returning signal light (see FIG. 1B), then an optical system much like that of the interrogation module 40 can be employed. Of course, a spectral grating and array detector (or other suitable spectrophotometric devices) would be substituted for the photodetector 64 (see FIG. 6B.), and the dichroic filter 66 (see FIG. 7A) would be omitted from the design.

Removal of low propagation angle light, as in the use of the obscuration 56 of FIG. 4, provides a number of advantages to surface plasmon resonance sensing operations. Low propagation angle light does not stimulate surface plasmon waves, except in metal films too thin to readily fabricate by currently available methods. In the case of back-reflected signal light from the mirror 122 of FIG. 1B, low propagation angle light is essentially signal noise which partly obscures the resonance effect to be measured. The reflector portion 26 of the sensing element 22 also advantageously adjusts lower propagation angle light to higher propagation angles.

Figure 2A:
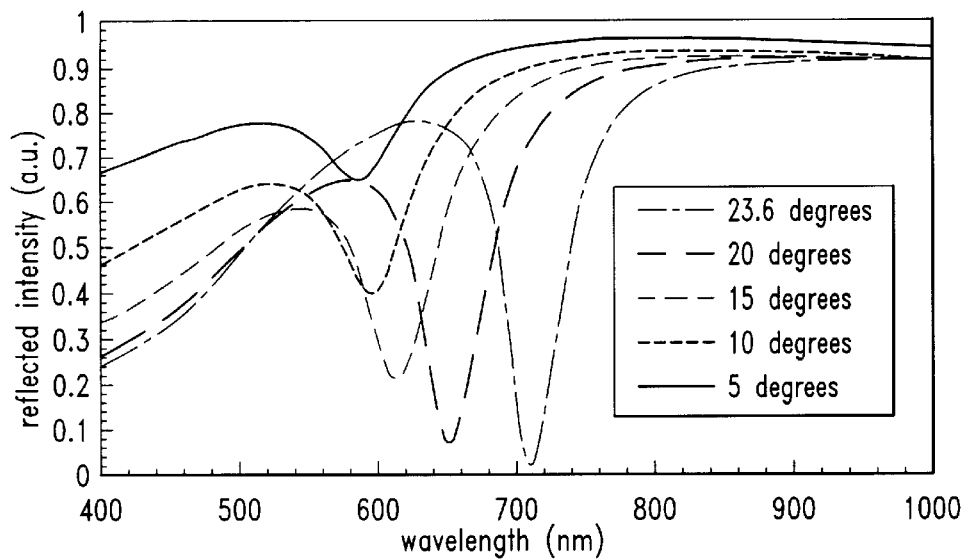
FIGS. 2A and 2B are graphs which depict theoretical resonance curves associated with use of the optical fiber of FIG. 1B in surface plasmon resonance sensing operations in accordance with the prior art.
Figure 2B:
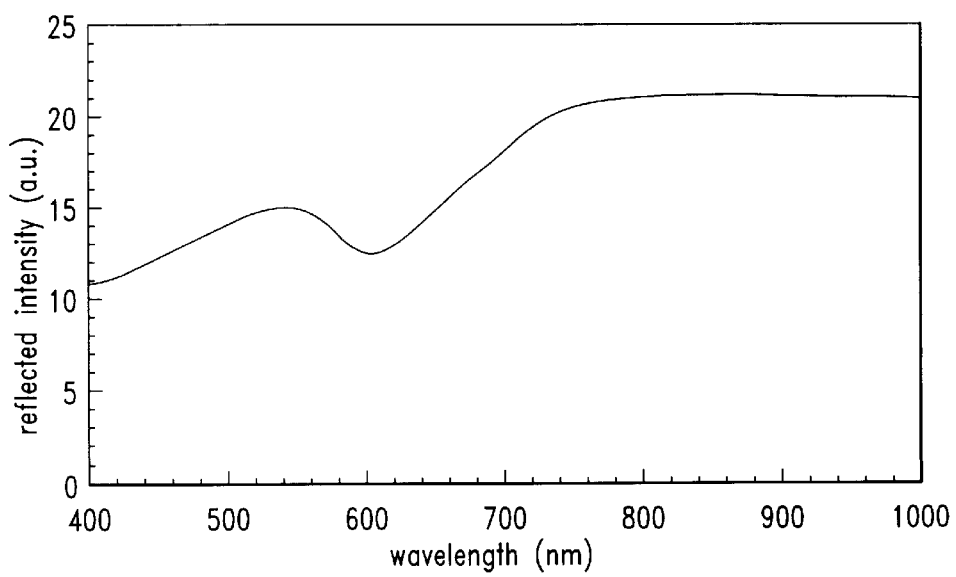
Figure 14:
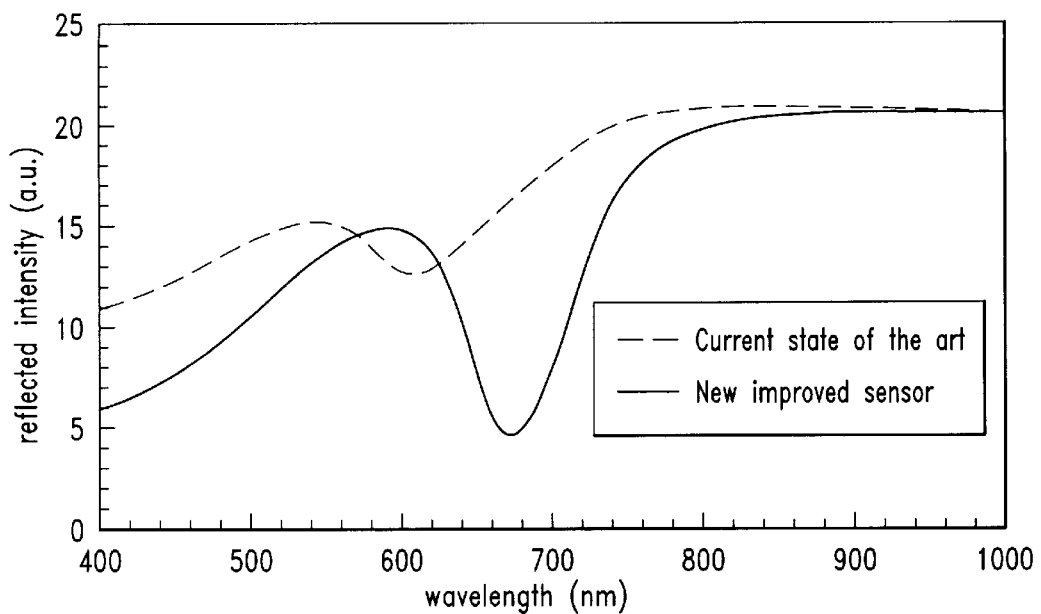
FIG. 14 is a graph which demonstrates the improved characteristics of a surface plasmon resonance sensor employing the optical sensing element of FIGS. 6A and 6B.

In accordance with ready adaptations of the embodiments described above, high numerical aperture light of approximately a constant propagation angle can be provided to a surface plasmon wave sensor. FIG. 14 shows the results of modeling a surface plasmon resonance sensor employing the optical features of the sensing element 22, as compared to the current state of the art (shown both in FIGS. 2B and 14). Assumed values include a silica optical fiber core of 400 μm having a 55 nm thick layer of gold, and a propagation angle of light of 21.60, relative to the optical axis of the fiber core, having a uniform dispersion of ±2°. The difference between the two curves illustrates the significant improvement afforded to surface plasmon resonance techniques by adaptation of the assay system described above.

Figure 15:
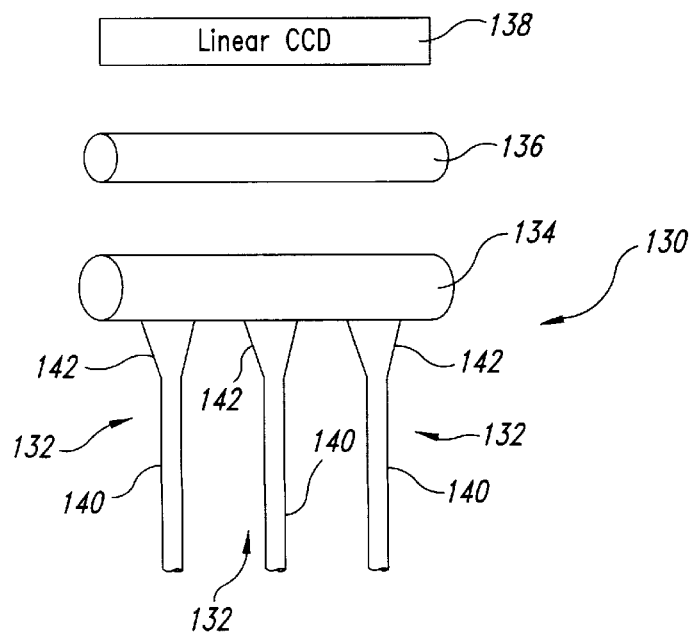
FIG. 15 depicts a multi-element sensor in accordance with an embodiment of the present invention.

It will be appreciated that, although embodiments of the invention have been described for purposes of illustration, various modifications may be made without deviating from the spirit and scope of the invention. For example, FIG. 15 depicts a multi-element sensor 130 having a plurality of approximately parallel sensing elements 132 formed as a single unit in combination with a single cylindrical lens portion 134. The cylindrical lens portion 134 is functionally substituted for the lens portion 24 described above; a cylindrical lens 136 is functionally substituted for the sapphire ball lens 62; and, an array of photodiodes or a linear charge-coupled device 138 is functionally substituted for the photodetector 64. The sensing elements 132 each include a slab waveguide portion 140 and two-dimensional reflector portion 142, with reflecting side surfaces defined mathematically like the reflective surface 27 described above. Advantages of the multi-element sensor 130 may include improved manufacturability, more flexible design parameters, improved waveguide power densities, and greater sensing surface area to test sample volume, thereby improving signal to noise characteristics.

As another example, any of a variety of lens configurations can be functionally substituted for the GRIN lens 52 described in connection with FIG. 4. Blocking low propagation angle light can be readily accomplished by a compound lens configuration, including paired planoconcave lenses forming highly collimated light, in which an obscuration is selectively positioned.

Particular optical structures, such as optical fibers, refractive surfaces and reflective surfaces have been described in connection with certain embodiments of the present invention. However, those skilled in the art will appreciate any number of light-directing media and devices which can be suitably adapted and combined to achieve the above-described effects and functions. For example, any of a wide variety of waveguides may be adapted for use as sensing elements. Also, metallized mirror reflecting surfaces may be substituted for the described dielectric surfaces. Reflective surfaces may be substituted for refractive surfaces, and vice versa.

The above-described embodiment of the reflector 26, whether alone or in combination with the lens 24, functions essentially as a light redirection device, which adjusts or otherwise modifies the propagation angle of light. The above-described embodiment of the light source module 34 includes, by virtue of features associated with the described lens 52 and obscuration 56, a light selection functionality in which certain ranges of light propagation angles may be blocked, passed, or otherwise selected for provision to subsequent light processing components. The above-described embodiments of the source fiber 38 and, in part, the sensing fiber 28 function as light transfer devices. Those skilled in the art will appreciate that a wide variety of alternative media, elements, and devices can be functionally substituted for these particular described embodiments.

Those skilled in the art will appreciate that various embodiments of the invention may be applied in fields other than assay methods and apparatus. Additionally, distinguishing between components such as a light source module and sensing element is somewhat arbitrary, since certain of the features described in connection with the sensing element could be suitably adapted to form a part of a light source module. Further, although the description above identifies "optical" features and effects, the invention encompasses any of a wide variety of equivalent features and effects associated with other parts of the electromagnetic spectrum, including light other than visible light.

These and other variations can be made to the invention in light of the detailed description above. In general, in the following claims, the terms used should not be construed to limit the invention to the specific embodiments disclosed in the specification, but should be construed to include all energy-directing media and devices that operate under the claims to provide associated signal transfer, retention, and detection characteristics. Accordingly, the invention is not limited by the disclosure, but instead its scope is to be determined entirely by the following claims.

What is claimed is:

1. An optical assay apparatus for detecting analytes in a sample, the apparatus comprising:

a light source module operable to produce light rays directed at a range of angles relative to an optical axis of the assay apparatus;

an optical sensor optically coupled with the light source module and including a ray redirection portion and a sensing fiber portion, the ray redirection portion operable to receive the light rays produced by the light source module and to correspondingly provide light rays directed at an approximately constant angle to the sensing fiber portion to correspondingly produce an evanescent electric field, the sensing fiber portion collecting light emitted from the sample in response thereto; and an interrogation module optically coupled with the optical sensor and operable to receive the collected light emitted from the sample.

2. The optical assay apparatus of claim 1 wherein the range of angles of the light rays produced by the light source module vary from angles greater than the minimum angle necessary to intercept the ray redirection portion to angles less than or equal to the maximum angle produced by the light source module.

3. The optical assay apparatus of claim 1 wherein the light source module includes an obscuration positioned relative to the optical axis to selectively block light rays directed at angles less than the minimum angle necessary to intercept the ray redirection portion.

4. The optical assay apparatus of claim 1 wherein the ray redirection portion and the sensing fiber portion of the optical sensor are formed together as a single piece.

5. The optical assay apparatus of claim 1 wherein the ray redirection portion of the optical sensor includes a refractive surface operable to collect the emitted light collected by the sensing fiber portion and provide the collected light to the interrogation module.

6. The optical assay apparatus of claim 1 wherein the ray redirection portion of the optical sensor includes a reflective surface operable to receive, as incident light, the light rays produced by the light source module and to provide, as reflected light, the light rays directed at an approximately constant angle to the sensing fiber portion.

7. The optical assay apparatus of claim 6 wherein the ray redirection portion of the optical sensor further includes a refractive surface operable to refract the light rays produced by the light source module.

8. The optical assay apparatus of claim 1 wherein the approximately constant angle is approximately less than a critical angle relative to the optical axis.

9. The optical assay apparatus of claim 1 wherein the optical sensor is coupled with the light source module by the interrogation module.

10. The optical assay apparatus of claim 9 wherein the interrogation module include s a window in which a portion of an optical fiber is embedded, the optical fiber transmitting the light rays produced by the light source module to the optical sensor.

11. The optical assay apparatus of claim 9 wherein the interrogation module includes a window in which a portion of an optical fiber is embedded, the optical fiber being coupled at a first end portion with the light source module to receive the light rays produced thereby, the optical fiber having a reflective surface at a second end portion, the reflective surface reflecting the light rays produced by the light source module to the optical sensor.

12. The optical assay apparatus of claim 9 wherein the interrogation module includes a window having a groove containing light absorbing material with a portion of an optical fiber embedded therein, the optical fiber transmitting the light rays produced by the light source module to the optical sensor.

13. An assay apparatus, comprising:
a light source module operable to produce light having a range of propagation angles; and
a sensor operable to receive the light produced by the light source module, the sensor including a light adjusting portion and an assay sensing portion, the light adjusting portion receiving the light produced by the light source module and providing light of a substantially constant propagation angle to the assay sensing portion, and the assay sensing portion comprising a waveguide.

14. The assay apparatus of claim 13 wherein the light produced by the light source module has a range of propagation angles from angles greater than the minimum angle necessary to intercept the ray redirection portion to angles less than or equal to the maximum angle produced by the light source module.

15. The assay apparatus of claim 13 wherein the assay sensing portion of the sensor includes a waveguide having a coating of sensor molecules, the light of the substantially constant propagation angle passing through the waveguide and creating an evanescent electric field in the coating of sensor molecules.

16. The assay apparatus of claim 13 wherein the assay sensing portion of the sensor includes an optical fiber core having a coating of sensor molecules, the light of the substantially constant propagation angle passing through the optical fiber core and creating an evanescent electric field in the coating of sensor molecules.

17. The assay apparatus of claim 13 wherein the assay sensing portion of the sensor includes a waveguide having a thin metallic coating, the light of the substantially constant propagation angle passing through the waveguide and exciting a surface plasmon wave on a surface of the metallic coating.

18. The assay apparatus of claim 13 wherein the assay sensing portion of the sensor includes an optical fiber core having a thin metallic coating, the light of the substantially constant propagation angle passing through the optical fiber core and exciting a surface plasmon wave on a surface of the metallic coating.

19. The assay system of claim 13, further comprising an interrogation module coupling the light source module with the sensor, the interrogation module including a window containing a waveguide, the waveguide transmitting the light produced by the light source module to the sensor.

20. The assay system of claim 13 wherein the light produced by the light source module is visible light.

21. An assay sensor, comprising:
a propagation angle modifier operable to receive the light having the range of propagation angles and to produce light having a substantially constant propagation angle; and
a waveguide coupled with the propagation angle modifier and operable to receive the light having the substantially constant propagation angle.

22. The sensor of claim 21 wherein the propagation angle modifier and the waveguide are of one-piece construction.

23. The sensor of claim 21 wherein the propagation angle modifier includes a reflecting surface operable to receive as incident light the light having the range of propagation angles and to produce as reflected light the light having the substantially constant propagation angle.

24. The sensor of claim 23 wherein the propagation angle modifier further includes a refracting portion for refracting the light having the range of propagation angles prior to incidence upon the reflecting surface.

25. The sensor of claim 23 wherein the reflecting surface corresponds to a curve described in a polar coordinate system as $$r(\theta) = R(0) \cdot \frac{(1 - \cos(\theta_0))}{(1 - \cos(\theta + \theta_0))}.$$

26. The sensor of claim 21 wherein the substantially constant propagation angle corresponds to a critical angle of the waveguide.

27. The sensor of claim 21 wherein the substantially constant propagation angle is approximately less than a critical propagation angle of the waveguide.

28. The sensor of claim 21 wherein the light having a substantially constant propagation angle is light having a narrow range of propagation angles with an average propagation angle corresponding to the substantially constant propagation angle.

29. The sensor of claim 21 wherein the waveguide is a portion of an optical fiber.

30. The sensor of claim 21 wherein the light having a substantially constant propagation angle includes light having a wavelength in an optical portion of an electromagnetic wave spectrum.

31. An optical assay apparatus for detecting analytes in a sample, the apparatus comprising:
   a light source operable to produce excitation light; and
   a sensor positioned in proximity to the sample, the sensor being coupled with the light source to receive the excitation light and to correspondingly produce an electric field within a portion of the sample to cause production of the emitted light; and
   an interrogation module coupling the sensor with the light source and including a window through which the emitted light passes into the interrogation module, the window having a groove in which is positioned a waveguide carrying the excitation light.

32. The optical assay apparatus of claim 31 wherein the groove includes a light absorbing material in which the waveguide is embedded.

33. The optical assay apparatus of claim 31 wherein the waveguide includes an end portion from which the excitation light incident upon the sensor emerges.

34. The optical assay apparatus of claim 33 wherein the end portion includes a reflective surface.

35. The optical assay apparatus of claim 33 wherein the end portion includes a right-angle reflector.

36. The optical assay apparatus of claim 33 wherein the window further includes an obscuration positioned with respect to the end portion to substantially block back-reflected excitation light from passing into the interrogation module.

37. An optical device having an optical axis comprising a reflective surface operable to receive, as incident light, light directed at a plurality of propagation angles relative to the optical axis and to produce, as reflected light, light directed at a substantially constant propagation angle, wherein the reflective surface has a shape corresponding to a curve described in a polar coordinate system as $$r(\theta) = R(0) \cdot \frac{(1 - \cos(\theta_0))}{(1 - \cos(\theta + \theta_0))}.$$

38. An optical device having an optical axis, comprising a reflective surface operable to receive, as incident light, light directed at a plurality of propagation angles relative to the optical axis and to produce, as reflected light, light directed at a substantially constant propagation angle, wherein the reflective surface comprises a two-dimensional shape disposed symmetrically about the optical axis and described in the polar coordinate system as $$r(\theta) = R(0) \cdot \frac{(1 - \cos(\theta_0))}{(1 - \cos(\theta + \theta_0))}.$$

39. An optical device having an optical axis, comprising a reflective surface operable to receive, as incident light, light directed at a plurality of propagation angles relative to the optical axis and to produce, as reflected light, light directed at a substantially constant propagation angle, wherein the reflective surface comprises a three-dimensional shape disposed symmetrically about the optical axis and described in the polar coordinate system as $$r(\theta) = R(0) \cdot \frac{(1 - \cos(\theta_0))}{(1 - \cos(\theta + \theta_0))}.$$

* * * * *

UNITED STATES PATENT AND TRADEMARK OFFICE
CERTIFICATE OF CORRECTION

PATENT NO. : 6,136,611
DATED : October 24, 2000
INVENTOR(S) : E.W. Saaski et al.

It is certified that error appears in the above-identified patent and that said Letters Patent is hereby corrected as shown below:

ON THE TITLE PAGE

| COLUMN | LINE | ERROR |
|---|---|---|
| Item [56] Pg. 1, col. 2 | Refs. Cited (Foreign Pats., Item 1) | "0 535 690" should read --0 535 690A-- |
| [56] Pg. 1, col. 2 | Refs. Cited (Foreign Pats., Item 2) | "WO 90 09574" should read --WO 90 09574A-- |
| [56] Pg. 2, col. 2 | Refs. Cited (Other Publs., Item 9) | "Chemical electrode surface plasmon resonance sensor," should read --"Chemical electrode surface plasmon resonance sensor,"-- |
| 13 (Claim 2, | 11 line 3) | "vary" should read --varies-- |
| 13 (Claim 10, | 45 line 2) | "include s" should read --includes-- |
| 14 (Claim 19, | 38 line 1) | "13," should read --13-- |

UNITED STATES PATENT AND TRADEMARK OFFICE
CERTIFICATE OF CORRECTION

PATENT NO. : 6,136,611
DATED : October 24, 2000
INVENTOR(S) : E.W. Saaski et al.

It is certified that error appears in the above-identified patent and that said Letters Patent is hereby corrected as shown below:

| COLUMN | LINE | ERROR |
|---|---|---|
| 15 (Claim 31, | 25 line 3) | "light; and" should read --light;-- |
| 16 (Claim 37, | 6 line 1) | "axis comprising" should read --axis, comprising-- |

Signed and Sealed this

Twenty-ninth Day of May, 2001

Attest:

NICHOLAS P. GODICI

Attesting Officer    Acting Director of the United States Patent and Trademark Office

UNITED STATES PATENT AND TRADEMARK OFFICE
CERTIFICATE OF CORRECTION

PATENT NO.    : 6,136,611
DATED         : October 24, 2000
INVENTOR(S)   : Elric W. Saaski et al.

It is certified that error appears in the above-identified patent and that said Letters Patent is hereby corrected as shown below:

<u>Column 1,</u>
Line 2, the following two sentences should be inserted:

-- This invention was made with Government support under Grant/Contract Number N00014-95-C-2251 awarded by the Department of the Navy. The Government has certain rights in the invention. --

Signed and Sealed this

Thirtieth Day of July, 2002

*Attest:*

*Attesting Officer*

JAMES E. ROGAN
*Director of the United States Patent and Trademark Office*